(12) United States Patent
Van Citters et al.

(10) Patent No.: US 11,357,546 B2
(45) Date of Patent: Jun. 14, 2022

(54) DEVICE FOR ENABLING PLACEMENT OF INTRA-OSSEOUS INFUSION TOOLS IN THE UPPER EXTREMITY

(71) Applicant: IOMetry, Inc., Hanover, NH (US)

(72) Inventors: Douglas W. Van Citters, Hanover, NH (US); Alexander H. Slocum, Jr., Lebanon, NH (US); Steven D. Reinitz, Minneapolis, MN (US)

(73) Assignee: IOMETRY, INC., Hanover, NH (US)

( * ) Notice: Subject to any disclaimer, the term of this patent is extended or adjusted under 35 U.S.C. 154(b) by 41 days.

(21) Appl. No.: 15/218,040

(22) Filed: Jul. 24, 2016

(65) Prior Publication Data

US 2017/0020560 A1 Jan. 26, 2017

Related U.S. Application Data

(60) Provisional application No. 62/196,589, filed on Jul. 24, 2015.

(51) Int. Cl.
*A61B 17/34* (2006.01)
*A61B 90/00* (2016.01)

(52) U.S. Cl.
CPC .. *A61B 17/3472* (2013.01); *A61B 2017/3407* (2013.01); *A61B 2090/3937* (2016.02)

(58) Field of Classification Search
CPC .......... A61B 8/0841; A61B 2017/3407; A61B 2017/3411; A61B 17/1778; A61B 17/151;

(Continued)

(56) References Cited

U.S. PATENT DOCUMENTS 2,525,398 A * 10/1950 Collins .................... A61M 5/00
604/179
3,167,072 A * 1/1965 Hester .................... A61M 25/02
128/DIG. 26

(Continued)

FOREIGN PATENT DOCUMENTS

WO WO-2013009901 A2 * 1/2013 ......... A61B 17/1637

OTHER PUBLICATIONS

Bisbinas, I., Belthur, M., Said, H. et al. Knee Surg Sports Traumatol Arthr (2006) 14: 762. https://doi.org/10.1007/s00167-006-0038-5.*

(Continued)

*Primary Examiner* — Scott J Medway
(74) *Attorney, Agent, or Firm* — Lathrop GPM LLP

(57) ABSTRACT

Survival of patients suffering from many infections diarrheal diseases, including Ebola, as well as trauma and post-partum hemorrhage is improved with large-volume, parenteral, fluid replacement. In lieu of IVs, Intra-Osseous (IO) lines are placed with the help of a Humerus-Finder™, a one-piece guide that identifies the humeral head at the shoulder and allows for easy, safe, placement of an IO line. This guide enables healthcare providers and lay-providers to place IO lines and deliver fluids to infected persons without direct contact, limiting risk to providers. The Humerus-Finder™ makes early, potentially life-saving, supportive treatment available where large-volume fluid infusion can save lives and is useful in disaster medicine and emergency medicine when it is not possible to place an IV line rapidly and safely by helping first responders achieve IO access for delivery of fluid resuscitation in a safe, reliable manner.

15 Claims, 5 Drawing Sheets

(58) Field of Classification Search
CPC . A61B 17/17; A61B 2017/90; A61B 17/1684; A61B 17/3403; A61B 17/3472; A61B 17/1691; A61B 17/1764; A61B 17/1789; A61B 8/12; A61M 5/427

See application file for complete search history.

(56) References Cited

U.S. PATENT DOCUMENTS

| | | | | |
|---|---|---|---|---|
| 3,542,022 A * | 11/1970 | Bartnik | A61M 5/427 | 604/116 |
| 3,620,209 A * | 11/1971 | Kravitz | A61M 5/422 | 601/79 |
| 4,013,070 A * | 3/1977 | Harroff | A61F 5/0109 | 602/21 |
| 4,228,796 A * | 10/1980 | Gardiner | A61M 5/427 | 604/116 |
| 4,314,568 A * | 2/1982 | Loving | A61M 5/425 | 604/116 |
| 4,834,802 A * | 5/1989 | Prier | A61B 17/1322 | 604/113 |
| 4,966,589 A * | 10/1990 | Kaufman | A61M 25/02 | 128/DIG. 26 |
| 5,167,630 A * | 12/1992 | Paul | A61B 5/02233 | 128/DIG. 26 |
| 5,259,386 A * | 11/1993 | Sharkawy | A61B 8/0841 | 600/455 |
| 5,634,904 A * | 6/1997 | Battenfield | A61B 17/3403 | 434/272 |
| 5,681,320 A * | 10/1997 | McGuire | A61B 17/0401 | 606/104 |
| 5,733,262 A * | 3/1998 | Paul | A61B 17/3403 | 604/116 |
| 5,800,402 A * | 9/1998 | Bierman | A61M 25/02 | 128/DIG. 26 |
| 5,810,781 A * | 9/1998 | Bierman | A61M 25/02 | 128/DIG. 26 |
| 5,839,904 A * | 11/1998 | Bloom | G09B 23/285 | 434/268 |
| 5,868,711 A * | 2/1999 | Kramer | A61B 17/3472 | 604/136 |
| 6,074,364 A * | 6/2000 | Paul | A61B 17/3403 | 128/DIG. 26 |
| 6,254,605 B1 * | 7/2001 | Howell | A61B 17/1714 | 606/86 R |
| 6,283,942 B1 * | 9/2001 | Staehlin | A61M 5/3287 | 604/116 |
| 6,443,928 B1 * | 9/2002 | Francis | A61M 5/3287 | 604/115 |
| 7,468,048 B2 * | 12/2008 | Meehan | A61F 5/0104 | 602/13 |
| 7,899,528 B2 * | 3/2011 | Miller | A61B 17/3472 | 607/3 |
| 8,133,201 B1 * | 3/2012 | Hurtado | A61M 5/427 | 604/116 |
| 8,211,056 B2 * | 7/2012 | Cull | A61M 1/3653 | 604/115 |
| 8,241,253 B2 * | 8/2012 | Bracken | A61M 25/02 | 604/179 |
| 8,419,683 B2 | 4/2013 | Miller et al. | | |
| 8,603,078 B2 * | 12/2013 | Stefanchik | A61B 17/0218 | 600/102 |
| 8,734,455 B2 * | 5/2014 | Park | A61B 17/175 | 606/89 |
| 8,870,820 B2 * | 10/2014 | Murphy | A61M 5/427 | 604/116 |
| 8,974,410 B2 * | 3/2015 | Miller | A61B 17/3472 | 604/116 |
| 9,775,639 B2 * | 10/2017 | Hanson | A61B 17/3403 | |
| 9,895,514 B2 * | 2/2018 | Bierman | A61M 5/158 | |
| 9,901,688 B2 * | 2/2018 | Agee | A61M 5/427 | |
| 9,962,524 B2 * | 5/2018 | Andino | A61M 25/02 | |
| 10,272,211 B1 * | 4/2019 | Cooke | A61M 5/422 | |
| 10,470,778 B2 * | 11/2019 | Corrigan, Jr. | A61B 8/06 | |
| 2006/0142774 A1 * | 6/2006 | Metzger | A61B 17/155 | 606/79 |
| 2007/0049945 A1 * | 3/2007 | Miller | A61B 17/32002 | 606/86 R |
| 2007/0084742 A1 | 4/2007 | Miller et al. | | |
| 2007/0260182 A1 * | 11/2007 | Munday | A61M 5/427 | 604/116 |
| 2007/0270775 A1 * | 11/2007 | Miller | A61B 10/025 | 604/506 |
| 2008/0045906 A1 * | 2/2008 | Grissom | A61M 25/02 | 604/179 |
| 2008/0140014 A1 * | 6/2008 | Miller | A61M 39/0247 | 604/180 |
| 2009/0093761 A1 * | 4/2009 | Sliwa | A61B 17/3403 | 604/116 |
| 2009/0312706 A1 * | 12/2009 | Shantha | A61M 5/427 | 604/112 |
| 2010/0198153 A1 * | 8/2010 | Yang | A61M 5/427 | 604/116 |
| 2010/0247513 A1 * | 9/2010 | Agee | A61B 17/320036 | 424/94.67 |
| 2011/0125200 A1 * | 5/2011 | Hanson | A61B 17/1764 | 606/86 R |
| 2011/0152987 A1 * | 6/2011 | Wahlgren | A61N 1/0492 | 607/115 |
| 2012/0150268 A1 * | 6/2012 | Doherty | A61F 7/02 | 607/108 |
| 2013/0041345 A1 * | 2/2013 | Kilcoin | A61B 17/3472 | 604/506 |
| 2014/0058409 A1 * | 2/2014 | Bratlie | A61M 5/425 | 606/131 |
| 2015/0230822 A1 * | 8/2015 | Hanson | A61B 17/3403 | 600/424 |
| 2016/0287814 A1 * | 10/2016 | McManus | A61M 5/427 | |
| 2017/0020560 A1 * | 1/2017 | Van Citters | A61B 17/3472 | |
| 2017/0135722 A1 * | 5/2017 | Ben-Mocha | A61B 17/3472 | |
| 2017/0281074 A1 * | 10/2017 | D'Lima | A61B 5/4576 | |
| 2019/0231470 A1 * | 8/2019 | Fink | A61M 5/427 | |
| 2021/0212658 A1 * | 7/2021 | McGrath | A61B 8/4477 | |

OTHER PUBLICATIONS

Baize et al. (Apr. 16, 2014) "Emergence of Zaire Ebola Virus Disease in Guinea," N. Engl. J. Med. 371:1418-1425.

Bradfute et al. (2007) "Lymphocyte Death in a Mouse Model of Ebola Virus Infection," J. Infect Dis. 196(Suppl 2): S296-S304.

Chan et al. (Oct. 13, 2014) "WHO Director-General's speech to the Regional Committee for the Western Pacific: Dr Margaret Chan, Director-General of the World Health Organization, (delivered in her absence by Ian Smith, Executive Director of the Director-General's Office)," Keynote address to the Regional Committee for the Western Pacific, Sixty-fifth session. Manila, Philippines. Accessible on the Internet at URL: http://www.who.int/dg/speeches/2014/regional-committee-western-pacific/en, 4 pgs. [Last Accessed Feb. 7, 2018].

Cooper et al. (2007) "Intra-osseous access (EZ-IO) for resuscitation: UK military combat experience," J. R. Army Medical Corps. 153(4):314-6.

Fasina et al. (Oct. 9, 2014) "Transmission dynamics and control of Ebola virus disease outbreak in Nigeria, Jul. to Sep. 2014," Euro Surveill. 19(40):20920. pp. 1-8.

Fischer et al. (Aug. 26, 2014) "Protecting Health Care Workers From Ebola: Personal Protective Equipment is Critical but is Not Enough," Annals of Internal Medicine. 161(10):753-754.

Hotchkiss et al. (2005) "Prevention of Lymphocyte Apoptosis—A Potential Treatment of Sepsis," Clin. Infect Dis. 41 (Suppl 7):S456-S469.

Hutchinson et al. (2007) "Cytokine and Chemokine Expression in Humans Infected with Sudan Ebola Virus," J. Infect Dis. 196(Suppl 2):S357-S363.

Lamontagne et al. (Oct. 23, 2014) "Doing Today's Work Superbly Well—Treating Ebola with Current Tools," New Eng. J. Med. 371(17): 1565-1566.

(56) References Cited

OTHER PUBLICATIONS

Sifferlin (Oct. 9, 2014) "This is How Ebola Patients are Equipping Their Homes," Time Magazine. Accessible on the Internet at URL: http://time.com/3481394/equipping-homes-to-treat-ebola-patients, 4 pgs. [Last Accessed Feb. 7, 2018].
World Health Organization (Oct. 6, 2014) "What we know about transmission of the Ebola virus among Humans: Ebola Situation Assessment," Accessible on the Internet at URL: http://www.who.int/mediacentre/news/ebola/06-october-2014/en, 3 pgs. [Last Accessed Feb. 7, 2018].
World Health Organization (Oct. 10, 2014) "WHO: Ebola Response Roadmap Update," Accessible on the Internet at URL: http://apps.who.int/iris/bitstream/10665/136161/1/roadmapupdate10Oct14_eng.pdf, 4 pgs. [Last Accessed Feb. 7, 2018].
World Health Organization (Nov. 7, 1014) "WHO: Ebola Response Roadmap Situation Report Update," Accessible on the Internet at URL: http://apps.who.int/iris/bitstream/10665/137592/1/roadmapsitrep_7Nov2014_eng.pdf, 5 pgs. [Last Accessed Feb. 7, 2018].
International Patent Application No. PCT/US2020/042654, International Search Report and Written Opinion dated Nov. 5, 2020, 11 pgs.
"2017 The Science and Fundamentals of Intraosseous Vascular Access" (Teleflex Global Research and Scientific Services, a Division of Clinical and Medical Affairs) Nov. 2017 (Nov. 2017).

* cited by examiner

DEVICE FOR ENABLING PLACEMENT OF INTRA-OSSEOUS INFUSION TOOLS IN THE UPPER EXTREMITY

CROSS-REFERENCE TO RELATED APPLICATION

This application claims the benefit of priority to U.S. Patent Application No. 62/196,589 filed Jul. 24, 2015, the entire content of which is hereby incorporated by reference into this application.

BACKGROUND

The present invention relates to a device used to place, or used to assist in the placement of, intra-osseous infusion tools to deliver fluid resuscitation to those in need.

The World Health Organization (WHO) declared the Ebola outbreak in the West African countries of Sierra Leone, Guinea, and Liberia to be the "most severe, acute health emergency seen in modern times". Of the five strains of Ebolaviridae, the Zaire strain is responsible for the current epidemic. Individuals infected with Ebola Virus suffer from a constellation of symptoms similar to septic shock, including fever, malaise, severe watery diarrhea, and massive dehydration.

Healthcare workers (HCWs) are acutely at risk for Ebola given their role in screening for Ebola in the Emergency Room and caring for patients known to have the disease. One study found that, as of August, 2014, more than 170 HCWs have been infected with Ebola, and 80 of them have died. Another study found that of the 90 patients infected with Ebola being treated at an Ebola Treatment Center (ETC) in Conarky, Guinea, 20% of were healthcare workers. Further, over half of the first 20 people infected at the start of the EVD outbreak in Nigeria were healthcare workers, 9 of which had cared for the index case before the patient was identified as having Ebola. For the West African outbreak, as of Oct. 10, 2014, 418 (5%) of the 8376 confirmed cases of Ebola Virus Disease were found to be in healthcare workers. By Nov. 9, 2014, there had been 13,268 confirmed cases of EVD with 4960 deaths. While Personal Protective Equipment (PPE) is essential in mitigating the risk of infection while triaging and caring for patients who have EVD, individuals are not always known to be infected with Ebola Virus when presenting to the emergency department (ED). Also, in countries hardest hit by the current Ebola epidemic there is an insufficient supply of PPE for those working on the front lines.

Ebola Virus Disease (EVD) is caused by the Ebolaviridae, of which there are five different strains named after regions in which they were discovered: Zaire, Sudan, Ivory Coast, Bundibugyo, and Reston. Ebolaviridae are members of the viral family Filoviridae, which along with Marburg species are negative sense, single-stranded RNA viruses with helical nucleocapsids. EVD leads to death of the host in upwards of 50% of those infected due to massive release of cellular cytokines leading to remarkable fluid and electrolyte loss, followed by hemorrhage in the terminal stages of the disease. This case fatality rate, however, is in the untreated population, and supportive care with interferon and intravenous fluids could significantly reduce the number of deaths.

Severe electrolyte abnormalities have been measured in patients infected with Ebola Virus and other diarrheal diseases, most importantly sodium and potassium, as these govern the membrane potentials of numerous cells, including myocytes and neurons essential to normal physiologic function. It has been reported that in patients suffering from EVD who have lost ability to drink fluids, multiple intravenous lines are needed to maintain hydration; physicians with Medecins sans Frontiers have reported observing, in the current epidemic, that "many critically ill patients die without adequate IV fluid resuscitation". This need for supportive care places healthcare workers at significant risk; the placement of an IV line requires close contact with the patient, which is made more difficult by the patient's dehydrated state. Also, the use of needles increases the risk of transmission through needle sticks and contact with other bodily fluids.

Ebola is far from the only disease in which fluid resuscitation is an urgently desired treatment and in which a patient's dehydrated state may make placement of an IV line difficult; patient survival in many acute diarrheal illnesses is enhanced by fluid administration; Wikipedia reports one and a quarter million deaths due to acute diarrhea yearly in years without significant Ebola. For example, and not limitation, infectious diarrheal ailments for which fluid replacement forms an important part of treatment include infections with: *Vibrio cholerae*, rotavirus, norovirus, amoebic dysentery, *Clostridium difficile, E. Coli* O157:H7, *shigella, salmonella, campylobacter*, even *staphylococcus* species. Acute diarrhea can also be triggered by food allergies and toxins.

Intraosseous (IO) infusion can be utilized to deliver large quantities of fluid and electrolytes, and is often employed in the shock trauma setting. The fluid delivery rate through an IO device is comparable to an IV catheter, and IO infusion has been used in the battlefield when IV access is unobtainable due to limb trauma. Further, an IO line can be placed via minimal contact with the patient by a skilled provider in the sternum, humeral head, or proximal tibia. Skilled providers are few and far between in West Africa, and are not always available in other field medical emergency situations; there is need for a device to guide lay-caregivers in the placement of IO needles for delivering supportive care.

A further use for IO infusion is to help treat patients in a mass casualty incident, to help resuscitate women who have just given birth and have developed post-partum hemorrhage, or any other situation in which there are limited resources, limited trained staff, and there is need to deliver large amounts of parenteral fluid.

SUMMARY EXAMPLES

In summary, the alignment guide is to be placed on a patient, with reference to anatomical landmarks, to aid in the location and placement of intra-vascular or intra-osseous devices. It is easily manufactured from cardboard cutouts, or as a monolithic structure produced via injection molding, casting, or forming. It is able to be used on a wide range of patient body types and sizes. Because it provides an additional barrier on top of required personal protective equipment, the guide reduces the risk of transmission of disease between healthcare providers and patients. In one preferred embodiment, the cross-section of the device is shaped like an "X", where one segment of the "X" is a handle, and the other three segments form two symmetrical troughs, one of which engages with the patient's left arm when used on the "left" side of the alignment guide, and the adjacent trough is to be used for engagement with the contralateral side.

The common middle segment between the troughs has a slot or cutout, which engages and identifies the anatomy that is to receive the injection or intra-osseous device. The alignment guide may be ambidextrous in that it can be held in either hand by a caregiver, and used on either side of a patient's body, depending on which trough engages with the patient. An exemplary use of the alignment guide is placement on the shoulder, and engagement with the humerus and arm, to enable placement of an intra-osseous needle for infusion of fluids and resuscitation of a patient with Ebola Virus Disease. A further exemplary use of the alignment guide is in disaster situations such as earthquakes, tsunamis, tornadoes, or hurricanes, where patients could far outnumber caregivers, to allow for rapid delivery of sustained fluid resuscitation. A still further exemplary use of the alignment guide is in the case of post-partum hemorrhage or other situations where a patient is at risk for hypovolemic shock, where the alignment guide can be used to help deliver requisite resuscitative fluids.

BRIEF DESCRIPTION OF THE DRAWINGS

The present invention can best be understood in conjunction with the accompanying drawings/images, in which.

Figure 1:
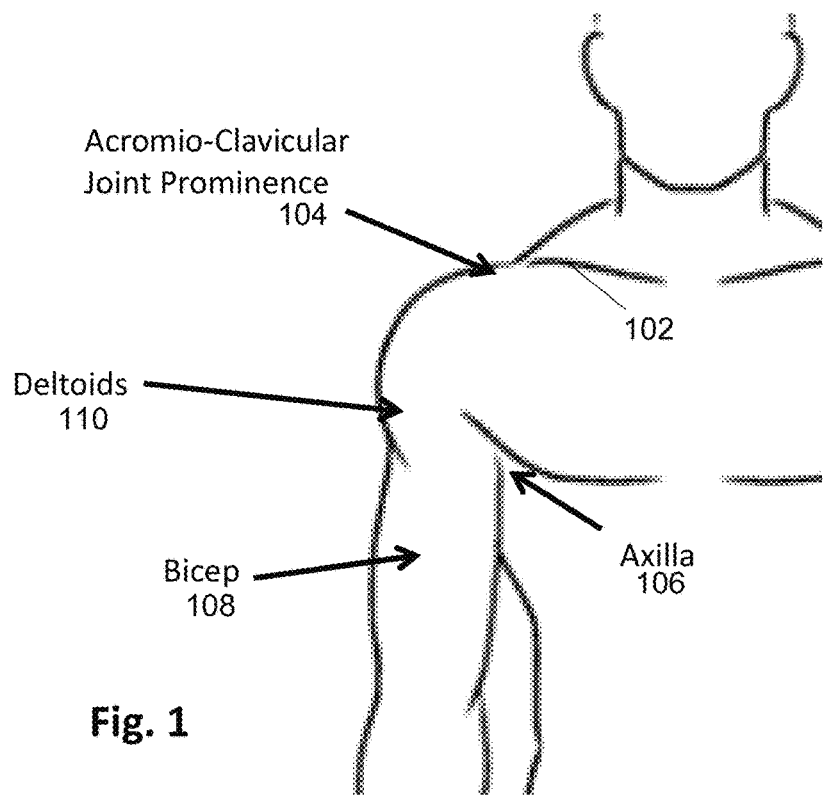
FIG. 1 is an anterior view sketch of relevant anatomy of the right upper extremity, showing surface anatomical landmarks.

In the drawings, preferred embodiments of the invention are illustrated by way of example, it being expressly understood that the description and drawings are only for the purpose of illustration and preferred designs, and are not intended as a definition of the limits of the invention.

DETAILED DESCRIPTION OF THE EMBODIMENTS

Applicant has observed that a desirable location for intraosseous (IO) infusion lines is in particular large-diameter portions of the humerus (upper arm bone) near the humeral head, but being careful to avoid dense cortical bone of the glennoid-humeral synovial joint. Applicant also has observed that location of this portion of the upper humerus by palpation, with sufficient precision to enter the desired site without risking joint involvement, is sometimes difficult for those medical personnel without extensive training. A principal object of the present device, therefore, is to provide a device that is to be placed on a patient to aid medical personnel in location and placement of intra-osseous devices into this large-diameter portion of the humerus.

The device engages, when placed on a patient, anatomical landmarks that locate the device in the proper position and orientation on a patient, and in various sizes is effectively useful on patients ranging in size from a small child to a large adult, and with a range of body styles from lean to obese; while minimizing need for direct contact between a caregiver and a patient, to mitigate the risk of transmission of communicable or otherwise infectious diseases. The device allows for ambidextrous use by caregivers and can be used on either side of the patient's body. The device is also easy to sanitize, and can be manufactured by a wide range of processes.

FIG. 1 is a sketch of the upper extremity with several anatomical structures labeled. Among these are the bony prominences of the clavicle 102, acromial-clavicular joint 104. Also important are the axilla 106 or armpit, and the soft-tissue bulges over the deltoid 110 and biceps 108.

Figure 2:
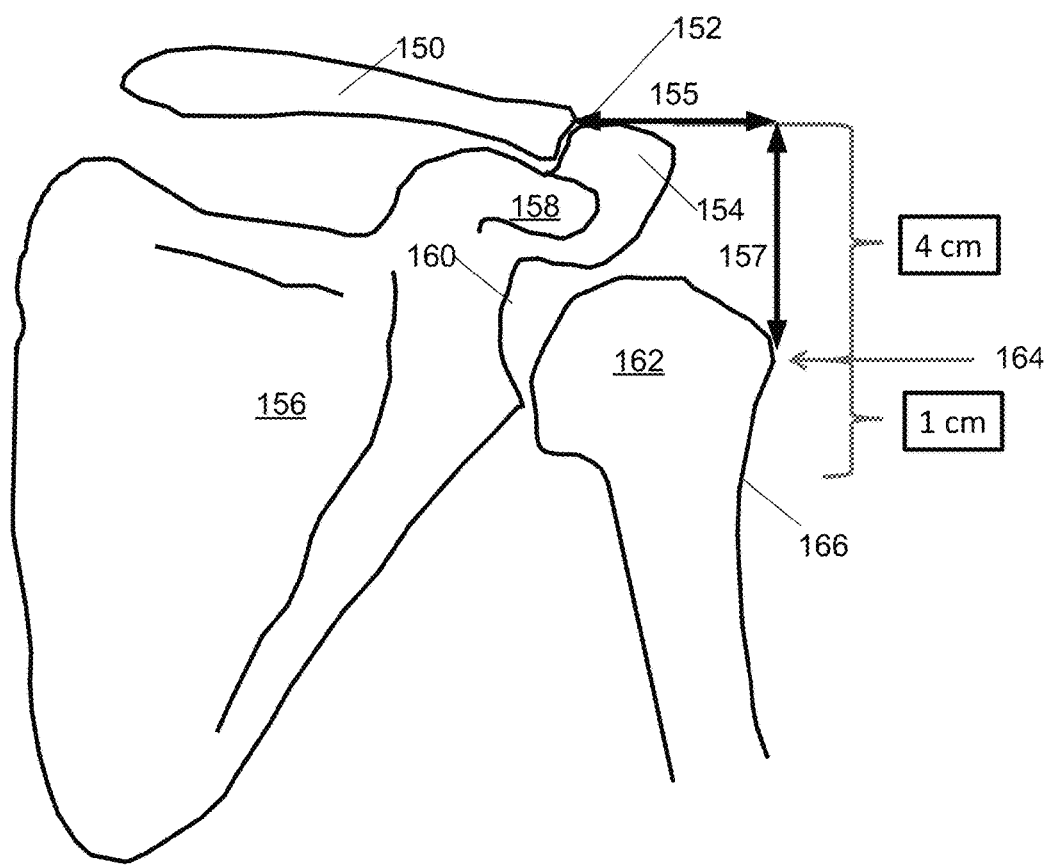
FIG. 2 is a posterior view sketch of bony anatomy of the right shoulder

FIG. 2 illustrates skeletal anatomy in posterior view of the right shoulder, showing clavicle 150, acromio-clavicular (AC) joint 152, acromion 154, scapula 156, coracoid 158, glenoid 160, and humerus 162 head. A desirable location 164 for starting an IO line is about a centimeter (cm) above the surgical neck 166 of the humerus, where the humerus head tapers into the humerus shaft; desirable location 164 is a distance 155, for adults approximately four centimeters below the top of the acromion 154, for distance ranges see table 1 below. The desirable location 164 is a distance 157, for adults ranging from four to six centimeters, lateral from the acromio-clavicular joint 152. It has been found that a distance from the axilla (armpit) to the desired insertion point is more variable, at 3-6 cm for children, 5-8 cm for teens, and 7-11 cm for adults.

A first embodiment of an alignment assistance device 200 (FIG. 3), or drill guide, has a first 202, and second locator arm 204, each arm having a length 223, with slot 206 between, adapted to being aligned over anatomic landmarks of the shoulder; the first and second locator arms are about 5 cm. long in a particular adult embodiment. Also, device 200 has a band 208 adapted to being positioned about an upper arm, including over biceps 108 (FIG. 1) and beneath axilla 106, the band coupled to the locator arms by a strap 211. Strap 211 has a locator hole 210 providing guidance for a proper location for starting an IO line, the locator hole centered a distance 225 above band 208. In a particular embodiment intended for use on adults, first 202 and second arm 204 are 5 centimeters long, and a distance 212 from a bend near the base of first 202 and second 204 arm to center of locator hole 212 is about four centimeters. Locator hole 210 is between two and three centimeters in diameter, in the same embodiment band 208 has width 221 approximately 14 (between 10 and 18) centimeters wide and extends a distance 219 of 25 to 40 centimeters in circumference to wrap around an upper arm. Band 208 may be formed of a springy material to conform to smaller arms by overlapping ends of band 208, or larger arms with a gap between ends 215, 217 of band 208.

A second embodiment of an alignment assistance device 250 (FIG. 4), or drill guide, has a first 252, and second locator arm 254, with slot 256 between, in a particular adult embodiment slot 256 has width 258 of about 2.5 centimeters. First 252 and second locator arm 254 are embossed or inked with arrows 260 that mark a level for inserting an IO line. First 252 and second arms 254 extend a distance 253 of 9-10 centimeters for an adult size (see table 1 for teen and child dimensions) above arrows 260, and slot 256 extends below arrows 260 by a distance 262 of approximately one centimeter, where arms 252, 254 merge into a strap 255, strap 255 has width approximately six centimeters and extends a distance 266 of about four to six centimeters for some particular embodiments to a line 268 at top of a band portion 270. Band portion has a length 271, and width 273, for dimensions see Table 1. Arms 252, 254 are adapted to being aligned over anatomic landmarks of the shoulder. Band portion 270 is adapted to being positioned about an upper arm, including over biceps 108 (FIG. 1) and beneath axilla 106. Band 270 portion is length 271 is adapted with ends 272, 274 and formation from a curved, springy material to conform to smaller arms by overlapping ends of band 270, or larger arms with a gap between ends 274, 272 of band 270. Band 270 also has a notch 276 of depth 278 about 5 centimeters and width 280 of about 2.5 centimeters.

Figure 3:
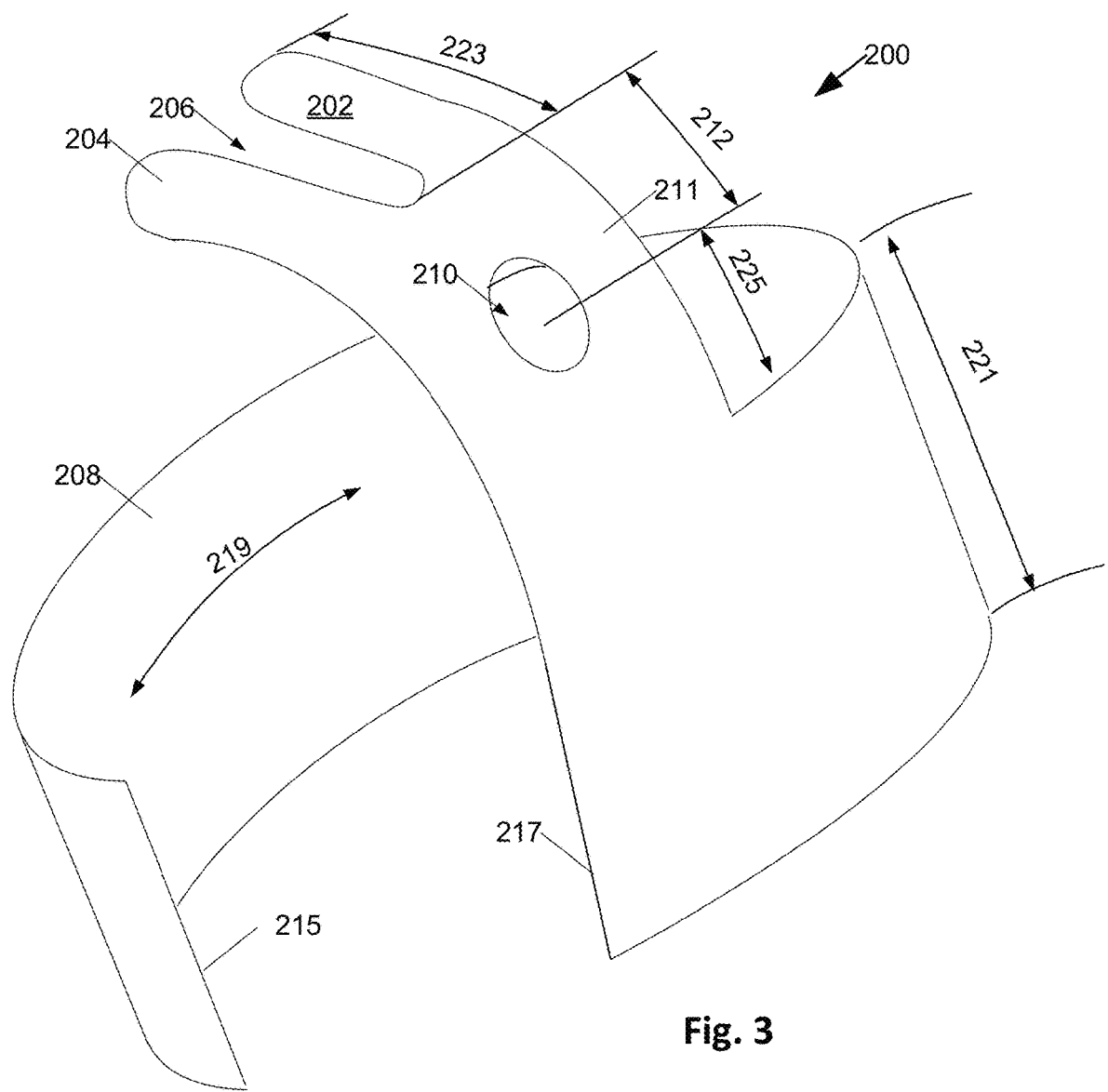
FIG. 3 is a perspective view of an embodiment of an alignment device.
Figure 4:
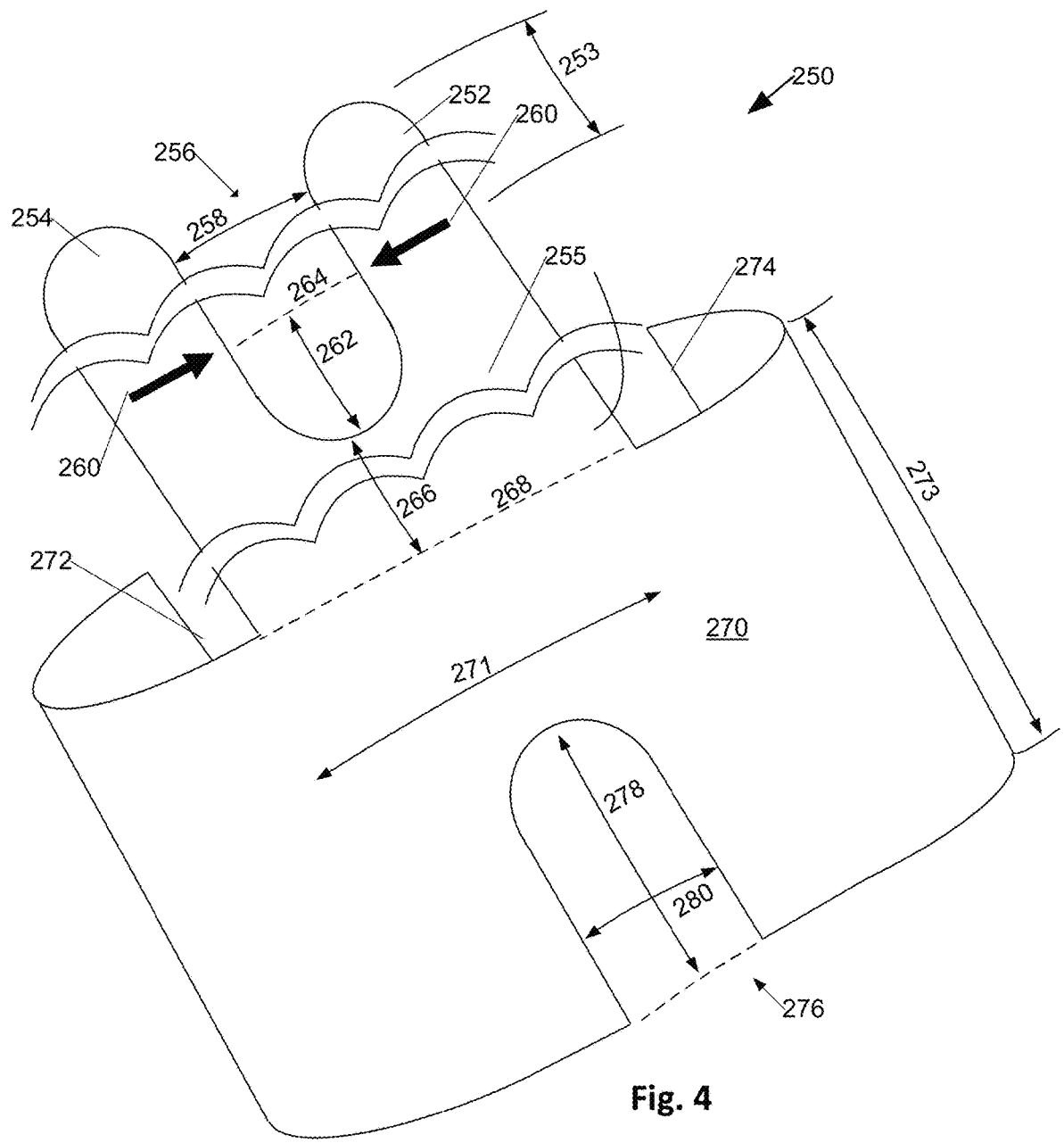
FIG. 4 is a perspective view of an alternative embodiment of the alignment device.
Figure 5:
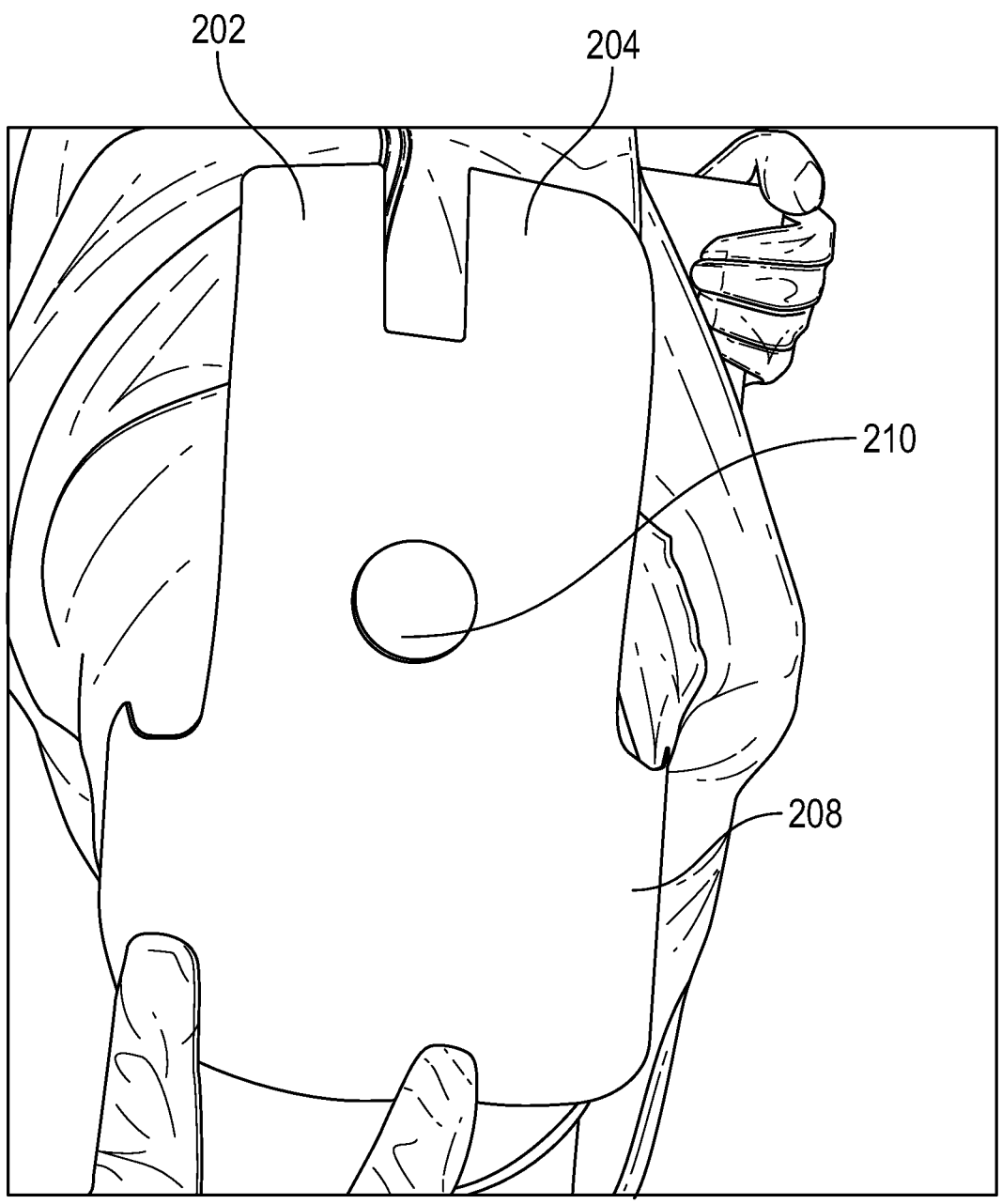
FIG. 5 is a photograph showing the alignment device of FIG. 3 in position around an upper arm of a subject.

Both embodiments of FIGS. 3 and 4 are fabricated from a springy bendable material such as polystyrene or ABS (acrylonitrile butadiene styrene) plastic, and sealed in gas-sterilized or radiation-sterilized envelopes. Alternatively, the embodiments may be fabricated of thin sheet stainless steel and heat sterilized in autoclavable envelopes. In use, both embodiments are positioned with band portions 208, 270, about a patient's upper arm as shown with the embodiment of FIG. 3 in FIG. 5, with arm lowered and hole 210 or slot 256 located over the lateral surface of the arm and locator arms 252, 254, 204, 202 over the top of patient's shoulder. With embodiments having lower slot 276, the slot is confirmed as lying over the humerus or anatomical markers, such as the point of the ulna at the elbow or the deltoid insertion, associated with the humerus to confirm device location. The alignment arrows 260 or locator hole 210 then indicate a proper location for IO line placement.

Figure 6:
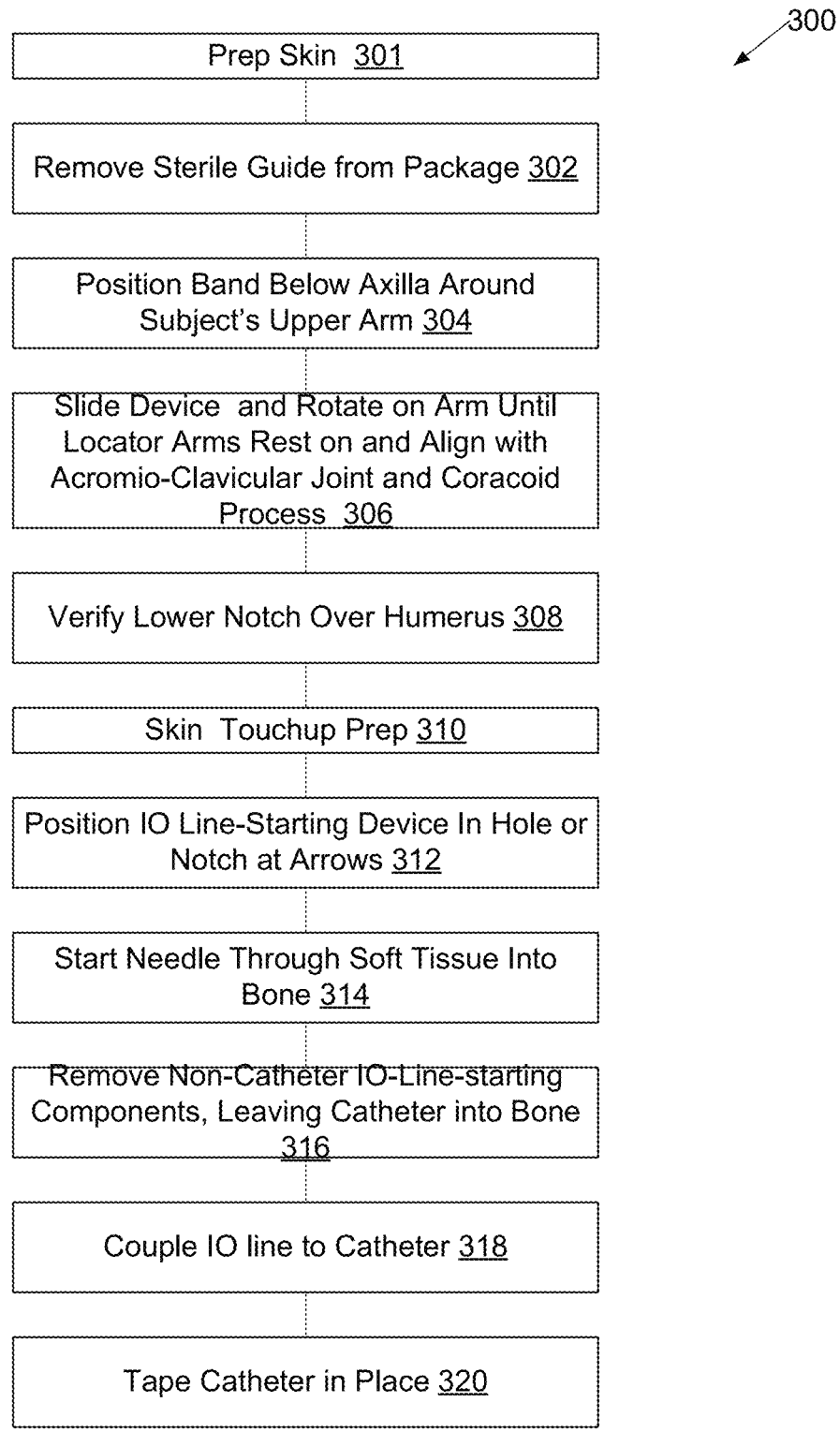
FIG. 6 is a flowchart illustrating a method of using the device of FIG. 3 or 4 to start an IO line.

The device is used according to the method 300 illustrated in FIG. 6. First, skin is prepped 301 with a suitable antiseptic, and the sterile device is removed 302 from its envelope and positioned 304 with band 208, 270 around the subject's arm, similar to positioning shown in FIG. 5. The device of FIG. 3 is then slid 306 along subject's arm until the locator arms 202, 204, 252, 254 are properly positioned, with the two arms located such that one arm is on each side of the acromio-clavicluar joint. In an alternative embodiment resembling that of FIG. 4, the device is slid along the upper arm while palpating through the bottom of notch 256 until the bottom of the notch is located at the surgical neck 166 of the humerus and the alignment arms cradle the humeral head. With embodiments having lower slot 276, the slot is verified 308 as lying over the humerus or anatomical markers, such as the point of the ulna at the elbow or the deltoid insertion, associated with the humerus to confirm device location and orientation. At this point, the skin prep may be touched up 310, and in some embodiments the device is taped into place to provide a firm support for securing the IO line. An IO delivery system is positioned 312 with needle centered in hole 210 or between embossed arrows 260, and penetrated 314 through soft tissue into humeral head bone. In some delivery systems, the drilling stylette (not shown) is removed 316, leaving a catheter portion in place extending from a cavity of the humerus. In some embodiments, the device is then removed from the subject's arm. The IO line is then coupled 318 to the catheter, and the catheter is taped 320 securely in place.

Applicant notes that the following distances are ranges for normal people of three age ranges, and of appropriate dimensions for the herein described alignment devices appropriate to use in normal people of those age ranges:

TABLE 1

Dimensions in Centimeters for Devices and Bony Structure

| Measurement | Child | Teen | Adult |
|---|---|---|---|
| 155 Acromio-clavicular joint to insertion point 164 | 3-4 cm | 4-5 cm | 4-6 cm |
| 157 top of acromion to insertion point Embodiments of FIG. 3 | 2-3 | 3-4 | 4-5 |
| 212 Alignment Hole Center to Alignment Arms (Strap Length) | 2-3 | 3-4 | 3-5 |
| 221 Band Width | 6-10 | 10-14 | 14-18 |
| 219 Band Length | 14-18 | 18-25 | 25-40 |
| 223 Alignment Arms Length | 5-6 | 6-7 | 7-8 |

TABLE 1-continued

Dimensions in Centimeters for Devices and Bony Structure

| Measurement | Child | Teen | Adult |
|---|---|---|---|
| 225 Alignment Hole Center Above Band Embodiments of FIG. 4 | 3-6 | 5-8 | 7-11 |
| 253 Arm Length Above Indicator Marks | 5-7 | 7-9 | 9-10 |
| 273 Band Width | 6-10 | 10-14 | 14-18 |
| 271 Band Length | 14-18 | 18-25 | 25-40 |
| 262 Markers Above Bottom of Notch | 0.5-1 | 0.8-1 | 1-1.5 |

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A location guidance device used to assist in the placement of intra-osseous infusion devices, comprising:
    a band adapted to fit about a subject's upper extremity below an axilla of the subject;
    a strap portion extending from, and perpendicular to, the band and forking into a locator structure comprising a first and a second locator arm, the first locator arm adapted to rest anterior to an anatomic landmark of the upper extremity of the subject, the second locator arm adapted to rest posterior to the anatomic landmark of the upper extremity of the subject; and
    a location indicator selected from the group consisting of (a) a hole in the strap portion and fully surrounded by material of the strap portion, and (b) marks on the locator arms;
    wherein the location indicator is positioned such that, when the first locator arm is positioned anterior to the anatomic landmark and the second locator arm is positioned posterior to the anatomic landmark, the location indicator geometrically indicates a location for starting an intraosseous line into a humerus of the subject where a head of the humerus tapers into a shaft of the humerus; and
    where the device is formed as one piece from a thin sheet of a springy, bendable, material.

2. The device of claim 1, wherein (a) the band has width between 10 and 18 centimeters and length between 14 and 40 centimeters, (b) the locator arms have length between 5 and 8 centimeters, and (c) the location indicator is the hole, and the hole is located between 3 and 8 centimeters below the locator arms.

3. The device of claim 2, wherein the anatomic landmark is an acromio-clavicular joint of the subject.

4. The device of claim 1, wherein (a) the band has width between 6 and 18 centimeters and length between 14 and 40 centimeters, (b) the locator arms have length between 5.5 and 11.5 centimeters, and (c) the location indicator is marks on the locator arms.

5. The device of claim 1, wherein the first locator arm is adapted to rest anterior to a humerus of the subject, and the second locator arm is adapted to rest posterior to the humerus of the subject.

6. The device of claim 1, wherein the location indicator is adapted to indicate a location for starting an intraosseous line into an upper humerus of the subject.

7. A method of starting an intraosseous line on a subject comprising:

positioning the band portion of the device of claim 2 around an upper extremity of the subject and aligning locator arms of the device such that they are positioned relative to anatomic landmarks on the upper extremity of the subject, the anatomic landmarks comprising over an acromio-clavicular joint, the device having the location indicator;

using an intraosseous line-starting device positioned with an intraosseous needle centered at the location indicator, penetrating the intraosseous needle through soft tissue into a humerus of the subject.

8. The method of claim 7, wherein the anatomic landmark is an acromio-clavicular joint of the subject.

9. The method of claim 7, the step of positioning further comprising taping the device into place.

10. A method of starting an intraosseous line on a subject comprising:

positioning a band portion of the device of claim 3 around the upper extremity of the subject;

sliding the device along the upper extremity of the subject until the first locator arm of the device is positioned anterior to an acromio-clavicular joint of the subject, and the second locator arm of the device is positioned posterior to the acromio-clavicular joint of the subject, with a bottom of a notch between the first and second locator arms approximately over a surgical neck of a humerus of the subject; and with an intraosseous line-starting device positioned with a needle centered at a location indicated by the location indicator, penetrating the needle through soft tissue into the humerus of the subject.

11. The device of claim 1, wherein the first and second locator arms are made of bendable material, and wherein the anatomic landmark is an acromio-clavicular joint.

12. The device of claim 1, wherein the anatomic landmark is an acromio-clavicular joint and the device is configured to position the location indicator on a lateral surface of the subject's upper arm when the first locator arm is positioned anterior to the acromio-clavicular joint and the second locator arm is positioned posterior to the acromio-clavicular joint.

13. The method of claim 7, wherein the anatomic landmark is the acromio-clavicular joint of the subject and the step of positioning includes positioning (a) the location indicator on a lateral surface of the subject's upper extremity, (b) the first locator arm anterior to the acromio-clavicular joint, and (c) the second locator arm posterior to the acromio-clavicular joint.

14. The device of claim 3, the location being between three and six centimeters from the acromio-clavicular joint.

15. The device of claim 1 having a slot adapted to be positioned over anatomical markers associated with the humerus while the locator arms are positioned with the first locator arm of the device anterior to the anatomic landmark of the upper extremity of the subject and the second locator arm posterior to the anatomic landmark of the upper extremity of the subject.

* * * * *